(12) United States Patent
Payen et al.

(10) Patent No.: US 12,398,362 B2
(45) Date of Patent: Aug. 26, 2025

(54) YEAST WITH IMPROVED ALCOHOL PRODUCTION

(71) Applicant: DANISCO US INC., Palo Alto, CA (US)

(72) Inventors: Celia Emily Gaby Payen, Wilmington, DE (US); Min Qi, Hockessin, DE (US)

(73) Assignee: DANISCO US INC., Palo Alto, CA (US)

( * ) Notice: Subject to any disclaimer, the term of this patent is extended or adjusted under 35 U.S.C. 154(b) by 415 days.

(21) Appl. No.: 16/619,565

(22) PCT Filed: Jun. 4, 2018

(86) PCT No.: PCT/US2018/035831
§ 371 (c)(1),
(2) Date: Dec. 5, 2019

(87) PCT Pub. No.: WO2018/226573
PCT Pub. Date: Dec. 13, 2018

(65) Prior Publication Data
US 2020/0131591 A1    Apr. 30, 2020

Related U.S. Application Data

(60) Provisional application No. 62/515,950, filed on Jun. 6, 2017.

(51) Int. Cl.
| | | |
|---|---|---|
| *C12N 1/14* | (2006.01) | |
| *C12N 1/18* | (2006.01) | |
| *C12N 9/90* | (2006.01) | |
| *C12N 15/81* | (2006.01) | |
| *C12P 7/06* | (2006.01) | |
| *C12P 7/10* | (2006.01) | |
| *C12R 1/85* | (2006.01) | |

(52) U.S. Cl.
CPC ............. *C12N 1/185* (2021.05); *C12N 1/18* (2013.01); *C12N 9/90* (2013.01); *C12N 15/81* (2013.01); *C12N 15/815* (2013.01); *C12P 7/06* (2013.01); *C12R 2001/85* (2021.05); *Y02E 50/10* (2013.01)

(58) Field of Classification Search
CPC .......... C12N 1/185; C12N 1/14; C12N 15/81; C12P 7/06; C12P 7/10
See application file for complete search history.

(56) References Cited

U.S. PATENT DOCUMENTS

| | | |
|---|---|---|
| 8,795,998 B2 | 8/2014 | Pronk et al. |
| 8,956,851 B2 | 2/2015 | Argyros et al. |
| 9,175,270 B2 | 11/2015 | Nevoigt et al. |

FOREIGN PATENT DOCUMENTS

| | | |
|---|---|---|
| WO | 2015148272 A1 | 10/2015 |
| WO | 2018089333 A1 | 5/2018 |

OTHER PUBLICATIONS

International Search Report and Written Opinion from PCT App. No. PCT/US2018/035831 dated Aug. 10, 2018, 10 pages.
Altschul et al., "Basic local alignment search tool", J Mol Biol., Oct. 1990, vol. 215, No. 3, pp. 403-410.
Altschul et al., "Local Alignment Statistics", Methods in Enzymology, vol. 266, 1996, pp. 460-480.
Arevelo-Rodriguez et al., "Cyclophilin A Is Localized to the Nucleus and Controls Meiosis in *Saccharoniyces cerevisae*", Eukaryotic Cell, vol. 4, No. 1, Jan. 2005, pp. 17-29.
Brown et al., "Cyclophilin A mediates Vid22p function in the import of fructose-1,6-bisphosphatase into Vid vesicles", J Biol Chem, vol. 276, 2001, pp. 48017-48026.
Davis E et al: "A yeast cyclophilin gene 1-10, essential for lactate metabolism at high 14-20, temperature", 23-26 Proceedings of the National Academy of Sciences, vol. 89, No. 23, Dec. 1992, pp. 11169-11173.
Devereux et al., "A comprehensive set of sequence analysis programs for the VAX", Nucleic Acids Research, Jan. 1984, vol. 12, No. 1, pp. 387-395.
Feng et al., "Progressive Sequence Alignment as a Prerequisite to Correct Phylogenetic Trees", J. Mol. Evol., vol. 25, 1987, pp. 351-360.
Hasumi et al., "Purification and properties of multiple molecular forms of yeast peptidy prolyl cis-trans isomerase", Biochim. Biophys. Acta, vol. 1161, 1993, pp. 161-167.
Henikoff et al., "Amino acid substitution matrices from protein blocks", Proc. Natl. Acad. Sci. USA, vol. 89, Nov. 1992, pp. 10915-10919.
Higgins et al., "Fast and sensitive multiple sequence alignments on a microcomputer", Cabios Communications, vol. 5, No. 2, 1989, pp. 151-153.
Karlin et al., "Applications and statistics for multiple high-scoring segments in molecular sequences", Proc. Natl. Acad. Sci. USA, vol. 90, Jun. 1993, pp. 5873-5877.
Kim et al: "Identification of novel genes responsible for ethanol and/or therniotolerance by transposon mutagenesis in *Saccharomyces cerevisiae*", Applied Microbiology and Biotechnology, vol. 91, No. 4, May 10, 2011, pp. 1159-1172.
Needleman et al., "A general method applicable to the search for similarities in the amino acid sequence of two proteins", J Mol Biol., Mar. 1970, vol. 48, No. 3, pp. 443-453.
Pearson et al., "Improved tools for biological sequence comparison", Proc. Natl. Acad. Sci. USA, Apr. 1988, vol. 85, No. 8, pp. 2444-2448.
Peterson, "Multiple SWItches to turn on chromatin", Curr. Opin. Genet. Dev., vol. 6, 1996, pp. 171-175.
Smith et al., "Comparison of biosequences", Advances in Applied Mathematics, Dec. 1981, vol. 2, Issue 4, pp. 482-489.

(Continued)

*Primary Examiner* — Maryam Monshipouri

(57) ABSTRACT

Described are compositions and methods relating to yeast cells having a genetic mutation that give rise to increased alcohol production. Such yeast is well-suited for use in alcohol production to reduce fermentation time and/or increase yields.

16 Claims, No Drawings

Specification includes a Sequence Listing.

(56) References Cited

OTHER PUBLICATIONS

Thompson et al., "Clustal W: improving the sensitivity of progressive multiple sequence alignment through sequence weighting, position-specific gap penalties and weight matrix choice", Nucleic Acids Res., vol. 22, No. 22, 1994, pp. 4673-4680.

Vandenbol et al., "Disruption of 12,13,22 six ORFs on *Saccharoniyces cerevisiae* chromisome X: the YJLO69c Gene of Unknown Function is Essential to Cell Viability", Yeast, vol. 15, Sep. 1999, pp. 1411-1417.

Winston et al., "Yeast SNF/SWI transcriptional activators and the SPT/SIN chromatin connection", Trends Genet., vol. 8, No. 11, Nov. 1992, pp. 387-391.

SEQUENCE LISTING

<160> NUMBER OF SEQ ID NOS: 3

<210> SEQ ID NO 1
<211> LENGTH: 162
<212> TYPE: PRT
<213> ORGANISM: Saccharomyces cerevisiae

<400> SEQUENCE: 1

```
Met Ser Gln Val Tyr Phe Asp Val Glu Ala Asp Gly Gln Pro Ile Gly
1               5                   10                  15

Arg Val Val Phe Lys Leu Tyr Asn Asp Ile Val Pro Lys Thr Ala Glu
            20                  25                  30

Asn Phe Arg Ala Leu Cys Thr Gly Glu Lys Gly Phe Gly Tyr Ala Gly
        35                  40                  45

Ser Pro Phe His Arg Val Ile Pro Asp Phe Met Leu Gln Gly Gly Asp
    50                  55                  60

Phe Thr Ala Gly Asn Gly Thr Gly Gly Lys Ser Ile Tyr Gly Gly Lys
65                  70                  75                  80

Phe Pro Asp Glu Asn Phe Lys Lys His His Asp Arg Pro Gly Leu Leu
                85                  90                  95

Ser Met Ala Asn Ala Gly Pro Asn Thr Asn Gly Ser Gln Phe Phe Ile
            100                 105                 110

Thr Thr Val Pro Cys Pro Trp Leu Asp Gly Lys His Val Val Phe Gly
        115                 120                 125

Glu Val Val Asp Gly Tyr Asp Ile Val Lys Lys Val Glu Ser Leu Gly
    130                 135                 140

Ser Pro Ser Gly Ala Thr Lys Ala Arg Ile Val Val Ala Lys Ser Gly
145                 150                 155                 160

Glu Leu
```

<210> SEQ ID NO 2
<211> LENGTH: 489
<212> TYPE: DNA
<213> ORGANISM: Saccharomyces cerevisiae

<400> SEQUENCE: 2

```
atgtcccaag tctattttga tgtcgaagct gatggccaac caattggccg tgtcgttttc      60
aagttgtaca acgacatagt cccaaagact gcagaaaact tcagagctct atgtaccggt     120
gaaaagggat tcggctacgc tggctctcca ttccacagag ttattccaga cttcatgttg     180
caaggtggta acttcactgc tggtaacggt accggcggta agtctatcta cggtggcaaa     240
ttcccagatg aaaacttcaa gaagcaccac gacagaccag gtttgttgtc catggccaac     300
gccggtccaa acaccaacgg ttctcaattc ttcatcacca ccgttccatg cccatggttg     360
gacggtaagc atgttgtctt tggtgaagtt gttgacggtt acgacatcgt taagaaggtt     420
gagtccttgg gttctccttc cggtgccacc aaggctagaa ttgttgttgc caagtccggt     480
gaattataa                                                             489
```

<210> SEQ ID NO 3
<211> LENGTH: 167
<212> TYPE: PRT
<213> ORGANISM: Saccharomyces cerevisiae

<400> SEQUENCE: 3

-continued

```
Met Asn Asn Glu Thr Ser Gly Lys Glu Thr Ala Ser Ala Pro Leu Cys
1               5                   10                  15

Ser Pro Lys Leu Pro Val Glu Lys Val Gln Arg Ile Ala Lys Asn Asp
            20                  25                  30

Pro Glu Tyr Met Asp Thr Ser Asp Asp Ala Phe Val Ala Thr Ala Phe
            35                  40                  45

Ala Thr Glu Phe Phe Val Gln Val Leu Thr His Glu Ser Leu His Arg
        50                  55                  60

Gln Gln Gln Gln Gln Gln Gln Val Pro Pro Leu Pro Asp Glu Leu
65                      70                  75                  80

Thr Leu Ser Tyr Asp Asp Ile Ser Ala Ala Ile Val His Ser Ser Asp
                85                  90                  95

Gly His Leu Gln Phe Leu Asn Asp Val Ile Pro Thr Thr Lys Asn Leu
            100                 105                 110

Arg Leu Leu Val Glu Glu Asn Arg Val Arg Tyr Thr Thr Ser Val Met
            115                 120                 125

Pro Pro Asn Glu Val Tyr Ser Ala Tyr Val Val Asn Asp Thr Ala Pro
            130                 135                 140

Lys Pro Asn Ile Val Glu Ile Asp Leu Asp Asn Asp Glu Asp Asp
145                 150                 155                 160

Glu Asp Val Thr Asp Gln Glu
                165
```

YEAST WITH IMPROVED ALCOHOL PRODUCTION

TECHNICAL FIELD

The present strains and methods relate to yeast having a genetic mutation that results in increased ethanol production. Such yeast is well-suited for use in alcohol production to reduce fermentation time and/or increase yields.

BACKGROUND

Many countries make fuel alcohol from fermentable substrates, such as corn starch, sugar cane, cassava, and molasses. According to the Renewable Fuel Association (Washington DC, United States), 2015 fuel ethanol production was close to 15 billion gallons in the United States, alone.

In view of the large amount of alcohol produced in the world, even a minor increase in the efficiency of a fermenting organism can result in a tremendous increase in the amount of available alcohol. Accordingly, the need exists for organisms that are more efficient at producing alcohol.

SUMMARY

Described are methods relating to modified yeast cells capable of increased alcohol production. Aspects and embodiments of the compositions and methods are described in the following, independently-numbered paragraphs.

1. In one aspect, modified yeast cells derived from parental yeast cells are provided, the modified cells comprising a genetic alteration that causes the modified cells to produce a decreased amount of functional Cpr1 polypeptide compared to the parental cells, wherein the modified cells produce during fermentation an increased amount of ethanol compared to parental cells under equivalent fermentation conditions.

2. In some embodiments of the modified cells of paragraph 1, the genetic alteration comprises a disruption of the YDR155c gene present in the parental cells.

3. In some embodiments of the modified cells of paragraph 2, disruption of the YDR155c gene is the result of deletion of all or part of the YDR155c gene.

4. In some embodiments of the modified cells of paragraph 2, disruption of the YDR155c gene is the result of deletion of a portion of genomic DNA comprising the YDR155c gene.

5. In some embodiments of the modified cells of paragraph 2, disruption of the YDR155c gene is the result of mutagenesis of the YDR155c gene.

6. In some embodiments of the modified cells of any of paragraphs 2-5, disruption of the YDR155c gene is performed in combination with introducing a gene of interest at the genetic locus of the YDR155c gene.

7. In some embodiments of the modified cells of any of paragraphs 1-6, the cells do not produce functional Cpr1 polypeptides.

8. In some embodiments of the modified cells of any of paragraphs 1-6, the cells do not produce Cpr1 polypeptides.

9. In some embodiments of the modified cells of any of paragraphs 1-8, the cells further comprise an exogenous gene encoding a carbohydrate processing enzyme.

10. In some embodiments, the modified cells of any of paragraphs 1-9 further comprise an alteration in the glycerol pathway and/or the acetyl-CoA pathway.

11. In some embodiments, the modified cells of any of paragraphs 1-10 further comprise an alternative pathway for making ethanol.

12. In some embodiments, the modified cells of any of paragraphs 1-11 further comprise a disruption of the YJL065 gene present in the parental cells.

13. In some embodiments of the modified cells of any of paragraphs 1-12, the cells do not produce functional Dls1 polypeptides.

14. In some embodiments of the modified cells of any of paragraphs 1-13, the cells are of a *Saccharomyces* spp.

15. In some embodiments of the modified cells of any of paragraphs 1-14, the amount of ethanol produced by the modified yeast cells and the parental yeast cells is measured at 24 hours following inoculation of a hydrolyzed starch substrate comprising 34-35% dissolved solids and having a pH of 4.8-5.4.

16. In another aspect, a method for producing a modified yeast cell is provided, comprising: introducing a genetic alteration into a parental yeast cell, which genetic alteration reduces or prevents the production of functional Cpr1 polypeptide compared to the parental cells, thereby producing modified cells that produces during fermentation an increased amount of ethanol compared to the parental cells under equivalent fermentation conditions.

17. In some embodiments of the method of paragraph 16, the genetic alteration comprises disrupting the YDR155c gene in the parental cells by genetic manipulation.

18. In some embodiments of the method of paragraph 16 or 17, the genetic alteration comprises deleting the YDR155c gene in the parental cells using genetic manipulation.

19. In some embodiments of the method of any of paragraphs 16-18, disruption of the YDR155c gene is performed in combination with introducing a gene of interest at the genetic locus of the YDR155c gene.

20. In some embodiments of the method of any of paragraphs 16-19, disruption of the YDR155c gene is performed in combination with making an alteration in the glycerol pathway and/or the acetyl-CoA pathway.

21. In some embodiments of the method of any of paragraphs 16-20, disruption of the YDR155c gene is performed in combination with adding an alternative pathway for making ethanol.

22. In some embodiments of the method of any of paragraphs 16-21, disruption of the YDR155c gene is performed in combination with disrupting the YJL065 gene present in the parental cells.

23. In some embodiments of the method of any of paragraphs 16-22, disruption of the YDR155c gene is performed in combination with introducing an exogenous gene encoding a carbohydrate processing enzyme.

24. In some embodiments of the method of any of paragraphs 16-23, the modified cell is from a *Saccharomyces* spp.

25. In some embodiments of the method of any of paragraphs 16-24, the amount of ethanol produced by the modified yeast cells and the parental yeast cells is measured at 24 hours following inoculation of a hydrolyzed starch substrate comprising 34-35% dissolved solids and having a pH of 4.8-5.4.

26. In another aspect, modified yeast cells produced by the method of any of paragraphs 16-25 are provided.

These and other aspects and embodiments of present modified cells and methods will be apparent from the description.

DETAILED DESCRIPTION

I. Overview

The present compositions and methods relate to modified yeast cells demonstrating increased ethanol production compared to their parental cells. When used for ethanol production, the modified cells allow for increased yields and or shorter fermentation times, thereby increasing the supply of ethanol for world consumption.

II. Definitions

Prior to describing the present strains and methods in detail, the following terms are defined for clarity. Terms not defined should be accorded their ordinary meanings as used in the relevant art.

As used herein, "alcohol" refer to an organic compound in which a hydroxyl functional group (—OH) is bound to a saturated carbon atom.

As used herein, "butanol" refers to the butanol isomers 1-butanol, 2-butanol, tert-butanol, and/or isobutanol (also known as 2-methyl-1-propanol) either individually or as mixtures thereof.

As used herein, "yeast cells" yeast strains, or simply "yeast" refer to organisms from the phyla Ascomycota and Basidiomycota. Exemplary yeast is budding yeast from the order Saccharomycetales. Particular examples of yeast are Saccharomyces spp., including but not limited to S. cerevisiae. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "variant yeast cells," "modified yeast cells," or similar phrases (see above), refer to yeast that include genetic modifications and characteristics described herein. Variant/modified yeast do not include naturally occurring yeast.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, WI); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | TUB |
| Delay divergent sequences %: | 40 |
| Gap separation distance: | 8 |
| DNA transitions weight: | 0.50 |
| List hydrophilic residues: | GP SNDQEKR |
| Use negative matrix: | OFF |
| Toggle Residue specific penalties: | ON |
| Toggle hydrophilic penalties: | ON |
| Toggle end gap separation penalty | OFF. |

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes proteins or strains found in nature.

As used herein, the term "protein of interest" refers to a polypeptide that is desired to be expressed in modified yeast. Such a protein can be an enzyme, a substrate-binding protein, a surface-active protein, a structural protein, a selectable marker, or the like, and can be expressed at high levels. The protein of interest is encoded by a modified endogenous gene or a heterologous gene (i.e., gene of interest") relative to the parental strain. The protein of interest can be expressed intracellularly or as a secreted protein.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences, but does not require the deletion of non-adjacent control elements.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, or any other method that abolishes gene expression. A gene can be disrupted by deletion or genetic manipulation of non-adjacent control elements.

As used herein, the terms "genetic manipulation" and "genetic alteration" are used interchangeably and refer to the alteration/change of a nucleic acid sequence. The alteration can include but is not limited to a substitution, deletion, insertion or chemical modification of at least one nucleic acid in the nucleic acid sequence.

As used herein, a "primarily genetic determinant" refers to a gene, or genetic manipulation thereof, that is necessary and sufficient to confer a specified phenotype in the absence of other genes, or genetic manipulations, thereof. However, that a particular gene is necessary and sufficient to confer a specified phenotype does not exclude the possibility that additional effects to the phenotype can be achieved by further genetic manipulations.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein, "attenuation of a pathway" or "attenuation of the flux through a pathway" i.e., a biochemical pathway, refers broadly to any genetic or chemical manipulation that reduces or completely stops the flux of biochemical substrates or intermediates through a metabolic pathway. Attenuation of a pathway may be achieved by a variety of well-known methods. Such methods include but are not limited to: complete or partial deletion of one or more genes, replacing wild-type alleles of these genes with mutant forms encoding enzymes with reduced catalytic activity or increased Km values, modifying the promoters or other regulatory elements that control the expression of one or more genes, engineering the enzymes or the mRNA encoding these enzymes for a decreased stability, misdirecting enzymes to cellular compartments where they are less likely to interact with substrate and intermediates, the use of interfering RNA, and the like.

As used herein, "aerobic fermentation" refers to growth in the presence of oxygen.

As used herein, "anaerobic fermentation" refers to growth in the absence of oxygen.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:
° C. degrees Centigrade
AA α-amylase
bp base pairs
DNA deoxyribonucleic acid
DP degree of polymerization
ds or DS dry solids
EtOH ethanol
g or gm gram
g/L grams per liter
GA glucoamylase
GAU/g ds glucoamylase units per gram dry solids
$H_2O$ water
HPLC high performance liquid chromatography
hr or h hour
kg kilogram
M molar
mg milligram
mL or ml milliliter
ml/min milliliter per minute
mM millimolar
N normal
nm nanometer
PCR polymerase chain reaction
ppm parts per million
SAPU/g ds protease units per gram dry solids
SSCU/g ds fungal alpha-amylase units per gram dry solids
Δ relating to a deletion
μg microgram
μL and μl microliter
μM micromolar

III. Modified Yeast Cells Having Reduced or Eliminated Cpr1 Activity

In one aspect, modified yeast cells are provided, the modified yeast having a genetic alteration that causes the cells of the modified strain to produce a decreased amount of functional Cpr1 polypeptide (alternatively called Cpr1p or YDR155c polypeptide) compared to the otherwise-identical parental cells. Cpr1 is a 162-amino acid peptidyl-prolyl cis-trans isomerase that accelerate the folding of proteins. Cpr1 localizes to the nucleus and is believed to have multiple roles in chromatin structure, cell division and transport (Hasumi, H. and Nishikawa, T. (1993) *Biochim. Biophys. Acta* 1161:161-67; Brown, C. R. et al., (2001) *J. Biol. Chem.* 276:48017-26 and Arevalo-Rodriguez, M. and Heitman, J. (2005) *Eukaryot. Cell* 4:17-29.

Applicants have discovered that yeast having a genetic alteration that affects Cpr1 function demonstrate increased ethanol production in fermentations, allowing for higher yields, shorter fermentation times or both. Shorter fermentation times allow alcohol production facilities to run more fermentation in a given period of time, increasing productivity. Shorter fermentation times and higher fermentation temperatures also reduce the risk of contamination during fermentation and, depending on ambient conditions, reduce the need to cool the fermentation reaction to maintain the viability of the yeast.

The reduction in the amount of functional YDR155c protein can result from disruption of the YDR155c gene present in the parental strain. Because disruption of the YDR155c gene is a primary genetic determinant for conferring the increased ethanol-production-phenotype to the modified cells, in some embodiments the modified cells need only comprise a disrupted YDR155c gene, while all other genes can remain intact. In other embodiments, the modified cells can optionally include additional genetic alterations compared to the parental cells from which they are derived. While such additional genetic alterations are not necessary to confer the described phenotype, they may confer other advantages to the modified cells.

Disruption of the YDR155c gene can be performed using any suitable methods that substantially prevent expression of a function YDR155c gene product, i.e., Cpr1. Exemplary methods of disruption as are known to one of skill in the art include but are not limited to: complete or partial deletion of the YDR155c gene, including complete or partial deletion of, e.g., the Cpr1-coding sequence, the promoter, the terminator, an enhancer, or another regulatory element; and complete or partial deletion of a portion of the chromosome that includes any portion of the YDR155c gene. Particular methods of disrupting the YDR155c gene include making nucleotide substitutions or insertions in any portion of the YDR155c gene, e.g., the Cpr1-coding sequence, the promoter, the terminator, an enhancer, or another regulatory element. Preferably, deletions, insertions, and/or substitutions (collectively referred to as mutations) are made by genetic manipulation using sequence-specific molecular biology techniques, as opposed to by chemical mutagenesis, which is generally not targeted to specific nucleic acid sequences. Nonetheless, chemical mutagenesis can, in theory, be used to disrupt the YDR155c gene.

Mutations in the YDR155c gene can reduce the efficiency of the YDR155c promoter, reduce the efficiency of a YDR155c enhancer, interfere with the splicing or editing of the YDR155c mRNA, interfere with the translation of the YDR155c mRNA, introduce a stop codon into the YDR155c-coding sequence to prevent the translation of full-length tYDR155c protein, change the coding sequence of the Cpr1 protein to produce a less active or inactive protein or reduce Cpr1 interaction with other nuclear protein components, or DNA, change the coding sequence of the Cpr1 protein to produce a less stable protein or target the protein for destruction, cause the Cpr1 protein to misfold or be incorrectly modified (e.g., by glycosylation), or interfere with cellular trafficking of the Cpr1 protein. In some embodiments, these and other genetic manipulations act to reduce or prevent the expression of a functional Cpr1 protein, or reduce or prevent the normal biological activity of Cpr1.

In some embodiments, the present modified cells include genetic manipulations that reduce or prevent the expression of a functional Cpr1 protein, or reduce or prevent the normal biological activity of Cpr1.

In some embodiments, the decrease in the amount of functional Cpr1 polypeptide in the modified cells is a decrease of at least 30%, at least 40%, at least 50%, at least 60%, at least 70%, at least 80%, at least 90%, at least 95%, at least 98%, at least 99%, or more, compared to the amount of functional Cpr1 polypeptide in parental cells growing under the same conditions. In some embodiments, the reduction of expression of functional Cpr1 protein in the modified cells is a reduction of at least 30%, at least 40%, at least 50%, at least 60%, at least 70%, at least 80%, at least 90%, at least 95%, at least 98%, at least 99%, or more, compared to the amount of functional Cpr1 polypeptide in parental cells growing under the same conditions.

In some embodiments, the increase in alcohol in the modified cells is an increase of at least 1%, at least 2%, at least 3%, at least 4%, at least 5%, or more, compared to the amount of alcohol produced in parental cells growing under the same conditions.

Preferably, disruption of the YDR155c gene is performed by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

In some embodiments, the parental cell that is modified already includes a gene of interest, such as a gene encoding a selectable marker, carbohydrate-processing enzyme, or other polypeptide. In some embodiments, a gene of introduced is subsequently introduced into the modified cells.

The amino acid sequence of the exemplified *S. cerevisiae* Cpr1 polypeptide is shown, below, as SEQ ID NO: 1:

MSQVYFDVEA DGQPIGRVVF KLYNDIVPKT AENFRALCTG

EKGFGYAGSP FHRVIPDFML QGGDFTAGNG TGGKSIYGGK

FPDENFKKHH DRPGLLSMAN AGPNTNGSQF FITTVPCPWL

DGKHVVFGEV VDGYDIVKKV ESLGSPSGAT KARIVVAKSG EL

Based on a BLAST search of the NCBI protein database, the described Cpr1 polypeptide is 100% identical to at least ten deposits:

The amino acid sequence information provided, herein, readily allows the skilled person to identify a Cpr1 protein, and the nucleic acid sequence encoding a Cpr1 protein, in any yeast, and to make appropriate disruptions in the YDR155c gene to affect the production of the Cpr1 protein.

In some embodiments, the decrease in the amount of functional Cpr1 polypeptide in the modified cells is a decrease of at least 30%, at least 40%, at least 50%, at least 60%, at least 70%, at least 80%, at least 90%, at least 95%, at least 98%, at least 99%, or more, compared to the amount of functional Cpr1 polypeptide in parental cells growing under the same conditions. In some embodiments, the reduction of expression of functional Cpr1 protein in the modified cells is a reduction of at least 30%, at least 40%, at least 50%, at least 60%, at least 70%, at least 80%, at least 90%, at least 95%, at least 98%, at least 99%, or more, compared to the amount of functional Cpr1 polypeptide in parental cells growing under the same conditions.

In some embodiments, the increase in ethanol production by the modified cells, compared to otherwise identical parental cells, is an increase of at least 0.2%, at least 0.4%, at least 0.6%, at least 0.8%, at least 1.0%, at least 1.2%, at least 1.4%, at least 1.6%, at least 1.8%, at least 2.0% or more.

TABLE 1

SEQ ID NO: 1 compared to other *S. cerevisiae* Cpr1 polypeptides

| Description | E value | % Identity | GenBank Accession No. |
| --- | --- | --- | --- |
| Cpr1p [*S. cerevisiae* S288c] | 2.8E−79 | 100% | NP_010439.1 |
| Cpr1p [*S. cerevisiae* VL3] | 2.8E−79 | 100% | EGA87502.1 |
| Cpr1p [*S. cerevisiae* AVRI796] | 2.8E−79 | 100% | EGA75445.1 |
| Cpr1p [*S. cerevisiae* RM11-1a] | 2.8E−79 | 100% | EDV08157.1 |
| Cpr1p [*S. cerevisiae* Kyokai No. 7] | 2.8E−79 | 100% | GAA22386.1 |
| Cpr1p [*S. cerevisiae* JAY291] | 2.8E−79 | 100% | EEU04638.1.1 |
| Cpr1p [*S. cerevisiae* FostersO] | 2.8E−79 | 100% | EGA63002.1 |
| Cpr1p [*S. cerevisiae* YJM789] | 2.8E−79 | 100% | EDN60494.1 |
| Cpr1p [*S. cerevisiae* Vin13] | 2.8E−79 | 100% | EGA79484.1 |
| Cpr1p [*S. cerevisiae* CEN.PK113-7D] | 2.8E−79 | 100% | EIW11359.1 |

It is expected that the present compositions and methods are applicable to other structurally similar Cpr1 polypeptides, as well as other related proteins, homologs, and functionally similar polypeptides.

In some embodiments of the present compositions and methods, the amino acid sequence of the Cpr1 protein that is altered in production levels has a specified degree of overall amino acid sequence identity to the amino acid sequence of SEQ ID NO: 1, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 1.

In some embodiments of the present compositions and methods, the YDR155c gene that is disrupted encodes a Cpr1 protein that has a specified degree of overall amino acid sequence identity to the amino acid sequence of SEQ ID NO: 1, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 1.

IV. Modified Yeast Cells Having Reduced Cpr1 Expression and Reduced Dls1 Expression In some embodiments, in addition to expressing decreased amounts of functional Cpr1 polypeptides, the present modified yeast cells further express reduced amounts of functional Dls1 polypeptides.

Dls1, encoded by YJL065c, is a 167-amino acid polypeptide subunit of the ISW2 yeast chromatin accessibility complex (yCHRAC), which contains Isw2, Itc1, Dpb3-like subunit (Dls1), and Dpb4 (see, e.g., Peterson, C. L. (1996) *Curr. Opin. Genet. Dev.* 6:171-75 and Winston, F. and Carlson, M. (1992) *Trends Genet.* 8:387-91). Applicants have determined that yeast having a genetic alteration that reduces the amount of functional Dls1 in the cell, in the absence of other genetic modifications, exhibit increased robustness in an alcohol fermentation, allowing higher-temperature, and potentially shorter, fermentations (data not shown).

Reduction in the amount of functional Dls1 produced in a cell can be accomplished by disruption of the YJL065c gene. Disruption of the YJL065c gene can be performed using any suitable methods that substantially prevent expression of a function YJL065c gene product, i.e., Dls1. Exemplary methods of disruption as are known to one of skill in the art include but are not limited to: complete or partial deletion of the YJL065c gene, including complete or partial deletion of, e.g., the Dls1-coding sequence, the promoter, the terminator, an enhancer, or another regulatory element; and complete or partial deletion of a portion of the chromosome that includes any portion of the YJL065c gene. Particular methods of disrupting the YJL065c gene include making nucleotide substitutions or insertions in any portion of the YJL065c gene, e.g., the Dls1-coding sequence, the promoter, the terminator, an enhancer, or another regulatory element. Preferably, deletions, insertions, and/or substitutions (collectively referred to as mutations) are made by genetic manipulation using sequence-specific molecular biology techniques, as opposed to by chemical mutagenesis, which is generally not targeted to specific nucleic acid sequences. Nonetheless, chemical mutagenesis can, in theory, be used to disrupt the YJL065c gene.

Mutations in the YJL065c gene can reduce the efficiency of the YJL065c promoter, reduce the efficiency of a YJL065c enhancer, interfere with the splicing or editing of the YJL065c mRNA, interfere with the translation of the YJL065c mRNA, introduce a stop codon into the YJL065c-coding sequence to prevent the translation of full-length tYJL065c protein, change the coding sequence of the Dls1 protein to produce a less active or inactive protein or reduce Dls1 interaction with other nuclear protein components, or DNA, change the coding sequence of the Dls1 protein to produce a less stable protein or target the protein for destruction, cause the Dls1 protein to misfold or be incorrectly modified (e.g., by glycosylation), or interfere with cellular trafficking of the Dls1 protein. In some embodiments, these and other genetic manipulations act to reduce or prevent the expression of a functional Dls1 protein, or reduce or prevent the normal biological activity of Dls1.

In some embodiments, the present modified cells include genetic manipulations that reduce or prevent the expression of a functional Dls1 protein, or reduce or prevent the normal biological activity of Dls1, as well as additional mutations that reduce or prevent the expression of a functional Isw2, Itc1, or Dpb4 proteins or reduce or prevent the normal biological activity of Isw2, Itc1, or Dpb4 proteins. In some embodiments, the present modified cells include genetic manipulations that reduce or prevent the expression of a functional Dls1 protein, or reduce or prevent the normal biological activity of Dls1, while having no additional mutations that reduce or prevent the expression of a functional Isw2, Itc1, or Dpb4 proteins or reduce or prevent the normal biological activity of Isw2, Itc1, or Dpb4 proteins.

The amino acid sequence of the exemplified *S. cerevisiae* Dls1 polypeptide is shown, below, as SEQ ID NO: 3:

```
MNNETSGKET ASAPLCSPKL PVEKVQRIAK NDPEYMDTSD

DAFVATAFAT EFFVQVLTHE SLHRQQQQQQ QQVPPLPDEL

TLSYDDISAA IVHSSDGHLQ FLNDVIPTTK NLRLLVEENR

VRYTTSVMPP NEVYSAYVVN DTAPKPNIVE IDLDNDEDDD

EDVTDQE
```

Based on such BLAST and Clustal W data, it is apparent that the exemplified *S. cerevisiae* Dls1 polypeptide (SEQ ID NO: 3) share a very high degree of sequence identity to other known *S. cerevisiae* Dls1 polypeptides, as well as Dls1 polypeptides from other *Saccharomyces* spp. The present compositions and methods, are therefore, fully expected to be applicable to yeast cells containing such structurally similar polypeptides, as well as other related proteins, homologs, and functionally similar polypeptides.

In some embodiments of the present compositions and methods, the amino acid sequence of the Dls1 protein that is disrupted has an overall amino acid sequence identity to the amino acid sequence of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 3

Preferably, disruption of the YJL065c gene is performed by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

In some embodiments, the decrease in the amount of functional Dls1 polypeptide in the modified cells is a decrease of at least 30%, at least 40%, at least 50%, at least 60%, at least 70%, at least 80%, at least 90%, at least 95%, at least 98%, at least 99%, or more, compared to the amount of functional Dls1 polypeptide in parental cells growing under the same conditions. In some embodiments, the reduction of expression of functional Dls1 protein in the modified cells is a reduction of at least 30%, at least 40%, at least 50%, at least 60%, at least 70%, at least 80%, at least 90%, at least 95%, at least 98%, at least 99%, or more, compared to the amount of functional Dls1 polypeptide in parental cells growing under the same conditions.

In some embodiments, the additional increase in ethanol production by the modified cells, compared to cells that only have reduced Cpr1 expression, is an increase of at least 0.2%, at least 0.4%, at least 0.6%, at least 0.8%, at least 1.0%, at least 1.2%, at least 1.4%, at least 1.6%, at least 1.8%, at least 2.0% or more.

V. Combination of Decreased Cpr1 Expression with Other Mutations that Affect Alcohol Production In some embodiments, in addition to expressing decreased amounts of functional Cpr1 polypeptides, optionally in combination with reduced expression of functional Dls1 polypeptides, the present modified yeast cells further include additional modifications that affect ethanol production.

In particular embodiments the modified yeast cells include an artificial or alternative pathway resulting from the introduction of a heterologous phosphoketolase gene and a heterologous phosphotransacetylase gene. An exemplary phosphoketolase can be obtained from *Gardnerella vaginalis* (UniProt/TrEMBL Accession No.: WP_016786789). An exemplary phosphotransacetylase can be obtained from *Lactobacillus plantarum* (UniProt/TrEMBL Accession No.: WP_003641060).

The modified cells may further include mutations that result in attenuation of the native glycerol biosynthesis pathway, which are known to increase alcohol production. Methods for attenuation of the glycerol biosynthesis pathway in yeast are known and include reduction or elimination of endogenous NAD-dependent glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat.

No. 9,175,270 (Elke et al.), U.S. Pat. No. 8,795,998 (Pronk et al.) and U.S. Pat. No. 8,956,851 (Argyros et al.).

The modified yeast may further feature increased acetyl-CoA synthase (also referred to acetyl-CoA ligase) activity (EC 6.2.1.1) to scavenge (i.e., capture) acetate produced by chemical or enzymatic hydrolysis of acetyl-phosphate (or present in the culture medium of the yeast for any other reason) and converts it to Ac-CoA. This avoids the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like. A particularly useful acetyl-CoA synthase for introduction into cells can be obtained from *Methanosaeta concilii* (UniProt/TrEMBL Accession No.: WP_013718460). Homologs of this enzymes, including enzymes having at least 85%, at least 90%, at least 92%, at least 95%, at least 97%, at least 98% and even at least 99% amino acid sequence identity to the aforementioned acetyl-CoA synthase from *Methanosaeta concilii*, are also useful in the present compositions and methods.

In some embodiments the modified cells may further include a heterologous gene encoding a protein with $NAD^+$-dependent acetylating acetaldehyde dehydrogenase activity and/or a heterologous gene encoding a pyruvate-formate lyase. The introduction of such genes in combination with attenuation of the glycerol pathway is described, e.g., in U.S. Pat. No. 8,795,998 (Pronk et al.). However, in most embodiments of the present compositions and methods, the introduction of an acetylating acetaldehyde dehydrogenase and/or a pyruvate-formate lyase is not required because the need for these activities is obviated by the attenuation of the native biosynthetic pathway for making Ac-CoA that contributes to redox cofactor imbalance. Accordingly, embodiments of the present compositions and methods expressly lack a heterologous gene(s) encoding an acetylating acetaldehyde dehydrogenase, a pyruvate-formate lyase or both.

In some embodiments, the present modified yeast cells further comprise a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, and/or substitution in one or more endogenous polynucleotides encoding FRA2, ALD6, ADH1, GPD2, BDH1, and YMR226C.

GOI Section

VI. Combination of Decreased Cpr1 Expression with Other Beneficial Mutations In some embodiments, in addition to expressing reduced amounts of Cpr1 polypeptides, optionally in combination with other genetic modifications that benefit alcohol production, the present modified yeast cells further include any number of additional genes of interest encoding proteins of interest. Additional genes of interest may be introduced before, during, or after genetic manipulations that result in reduced expression of Cpr1 polypeptides. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transladolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VII. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces, Lachancea* and *Schizosaccharomyces* spp. Numerous yeast strains are commercially available, many of which have been selected or genetically engineered for desired characteristics, such as high alcohol production, rapid growth rate, and the like. Some yeasts have been genetically engineered to produce heterologous enzymes, such as glucoamylase or α-amylase.

VIII. Substrates and Products

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

These and other aspects and embodiments of the present strains and methods will be apparent to the skilled person in view of the present description. The following examples are intended to further illustrate, but not limit, the strains and methods.

EXAMPLES

Example 1. Deletion of YDR155c in *Saccharomyces cerevisiae*

Genetic screening was performed to identify *S. cerevisiae* mutants capable of improved ethanol production after 24 hours of fermentation, and a number of candidate genes were identified and selected for further testing (data not shown). One of the genes selected for further analysis was YDR155c, which encodes Cpr1. The amino acid sequence of Cpr1 is provided below as SEQ ID NO: 1:

```
MSQVYFDVEA DGQPIGRVVF KLYNDIVPKT AENFRALCTG

EKGFGYAGSP FHRVIPDFML QGGDFTAGNG TGGKSIYGGK

FPDENFKKHH DRPGLLSMAN AGPNTNGSQF FITTVPCPWL

DGKHVVFGEV VDGYDIVKKV ESLGSPSGAT KARIVVAKSG EL
```

Using standard yeast molecular biology techniques, the YDR155c gene was disrupted by deleting essentially the entire coding sequence for Cpr1, i.e., by deleting the nucleic acid sequence from 4 base-pair before the start codon to 10 base-pairs before the stop codon in both alleles of *S. cerevisiae*. All procedures were based on the publically available nucleic acid sequence of YDR155c, which is provided below as SEQ ID NO: 2 (5' to 3'):

```
ATGTCCCAAG TCTATTTTGA TGTCGAAGCT GATGGCCAAC

CAATTGGCCG TGTCGTTTTC AAGTTGTACA ACGACATAGT

CCCAAAGACT GCAGAAAACT TCAGAGCTCT ATGTACCGGT

GAAAAGGGAT TCGGCTACGC TGGCTCTCCA TTCCACAGAG

TTATTCCAGA CTTCATGTTG CAAGGTGGTG ACTTCACTGC

TGGTAACGGT ACCGGCGGTA AGTCTATCTA CGGTGGCAAA

TTCCCAGATG AAAACTTCAA GAAGCACCAC GACAGACCAG

GTTTGTTGTC CATGGCCAAC GCCGGTCCAA ACACCAACGG

TTCTCAATTC TTCATCACCA CCGTTCCATG CCCATGGTTG

GACGGTAAGC ATGTTGTCTT TGGTGAAGTT GTTGACGGTT

ACGACATCGT TAAGAAGGTT GAGTCCTTGG GTTCTCCTTC

CGGTGCCACC AAGGCTAGAA TTGTTGTTGC CAAGTCCGGT

GAATTATAA
```

The host yeast used to make the modified yeast cells was commercially available FERMAX™ Gold (Martrex, Inc., Chaska, MN, USA). Deletion of the YDR155c gene were confirmed by colony PCR. The modified yeast was grown in non-selective media to remove the plasmid conferring Kanamycin resistance used to select transformants, resulting in modified yeast that required no growth supplements compared to the parental yeast.

Example 2: Ethanol Production by Modified Yeast with Reduced Expression of Cpr1

FG-155c yeast harboring the deletion of the YDR155c gene was tested for its ability to produce ethanol compared to benchmark yeast (i.e., FERMAX™ Gold), which is wild-type for the YDR155c gene) in liquefact at 32 and 34° C. Liquefact (i.e., corn flour slurry having a dry solid (ds) value of 34.2% was prepared by adding 600 ppm urea, 0.124 SAPU/g ds FERMGEN™ 2.5× (an acid fungal protease), 0.33 GAU/g ds CS4 (a variant of *Trichoderma reesei* glucoamylase) and 1.46 SSCU/g ds *Aspergillus kawachii* α-amylase at pH 4.8.

50 grams of liquefact was weighted into 100 ml vessels and inoculated with fresh overnight cultures from colonies of the modified strain or FG strain at 32° and 34° C. Samples were harvested by centrifugation at 24 and 55 hrs, filtered through 0.2 μm filters, and analyzed for ethanol, glucose, acetate and glycerol content by HPLC (Agilent Technologies 1200 series) using Bio-Rad Aminex HPX-87H columns at 55° C., with an isocratic flow rate of 0.6 ml/min in 0.01 N $H_2SO_4$ eluent. A 2.5 μl sample injection volume was used. Calibration standards used for quantification included known amounts of DP4+, DP3, DP2, DP1, glycerol and ethanol. The results of the analyses are shown in Table 2. Ethanol increase is reported with reference to the FG strain.

TABLE 2

Analysis of fermentation broth following fermentation for 24 and 55 hrs

| Time (hrs) | Strain | Temp. (° C.) | Glucose (g/L) | Ethanol (g/L) | Increase in ethanol compared to FG (%) |
|---|---|---|---|---|---|
| 24 | FG | 32 | 44.10 | 108.35 | 1* |
| 24 | FG-155c | 32 | 34.79 | 110.22 | 1.7 |
| 24 | FG | 34 | 41.12 | 110.50 | 1* |
| 24 | FG-155c | 34 | 35.13 | 111.78 | 1.2 |
| 55 | FG | 32 | 0 | 146.62 | 1* |
| 55 | FG-155c | 32 | 0 | 146.20 | 1.0 |
| 55 | FG | 34 | 2.02 | 144.65 | 1* |
| 55 | FG-155c | 34 | 2.70 | 142.30 | 1.0 |

*nominal reference value

Yeast harboring the YDR155cc gene deletion produced significantly more (i.e., almost 1.2 to 1.7%) ethanol compared the unmodified reference strain under at both 32° and 34° C. at 24 hrs.

Example 3. Reduced Expression of Cpr1 in Combination with Reduced Expression of Dls1

An experiment was performed to determine if decreasing the amount of Cpr1 in combination with reducing the amount of Dls1 (encoded by the YJL065c gene) in yeast increase further increase tolerance and alcohol production compared to decrease Cpr1, alone. Using standard yeast molecular biology techniques, the YDR155c gene was disrupted by deleting essentially the entire coding sequence for Cpr1 in the aforementioned FG host yeast in which the deletion of YJL065c had been made (FG-65c). Yeast harboring the deletion of YJL065c and the Cpr1 deletion (FG-65c-155c) were tested for their ability to produce ethanol compared to the benchmark yeast in liquefact incubated at 32° C. Liquefact (i.e., corn flour slurry having a dry solid (ds) value of 34.1% was prepared by adding 600 ppm urea, 0.124 SAPU/g ds FERMGEN™ 2.5× (an acid fungal protease), 0.33 GAU/g ds CS4 (a variant of *Trichoderma reesei* glucoamylase) and 1.46 SSCU/g ds *Aspergillus kawachii* α-amylase at pH 4.8.

50 grams of liquefact was weighted into 250 ml vessels and inoculated with fresh overnight cultures from colonies of the FG-65c and FG-65c-155c strain and incubated at 32° C. for 24 hrs. A gas monitoring system (ANKOM Technology) was used to record the rate of fermentation based on cumulative pressure following $CO_2$ production over time. Samples were harvested by centrifugation, filtered through 0.2 µm filters, and analyzed for ethanol, glucose, acetate and glycerol content by HPLC (Agilent Technologies 1200 series) using Bio-Rad Aminex HPX-87H columns at 55° C., with an isocratic flow rate of 0.6 ml/min in 0.01 N $H_2SO_4$ eluent. A 2.5 µl sample injection volume was used. Calibration standards used for quantification included known amounts of DP4+, DP3, DP2, DP1, glycerol and ethanol. The results of the analyses are shown in Table 3. Ethanol increase at 24 hrs is reported with reference to the FG-65c strain.

TABLE 3

Analysis of fermentation broth for 24 hrs with FG, FG-65c and FG-65c-155c yeast

| Temperature (° C.) | Strain | Glucose (g/L) | Glycerol (g/L) | Ethanol (g/L) | Ethanol increase (%) |
|---|---|---|---|---|---|
| 32 | FG-65c | 51.69 | 13.01 | 106.12 | 1* |
| 32 | FG-65c-155c | 44.88 | 13.57 | 109.13 | 2.8 |
| 32 | FG | 52.05 | 13.08 | 108.20 | — |

*nominal reference value

Yeast harboring the deletion of the gene YDR155c in addition to the deletion of the gene DLS1 (YJ065c) produced significantly more ethanol (i.e., up to 2.8%) compared to the strain harboring the gene deletion of DLS1 alone at 24 hrs. Note that the FG-65c yeast ultimately produce more ethanol at 48 hours that wild-type FG yeast (data not shown); however, they are relatively "slow starters" and produce less ethanol at 24 hours. Deletion of the YDR155c gene therefore appears to increase the initial growth rate of the FG-65c yeast.

Example 4: Ethanol Production by Modified Yeast Having an Alternative Ethanol Pathway Yeast harboring the deletion of the gene YDR155c and further expressing an alternative pathway to produce ethanol (i.e., by expressing a heterologous phosphoketolase, a heterologous phosphotransacetylase, and an acetylating acetaldehyde dehydrogenase, as described in international patent application WO 2015/148272 (Miasnikov et al.)), were tested for their ability to produce ethanol compared to parental yeast, which included the alternative ethanol pathway but did not have a deletion of gene YDR155c. In this case, the parental yeast is designated "GPY10009" and the modified yeast is designated "GPY10009-155c." Assay conditions and procedures were as described in the previous Examples. Samples were analyzed for ethanol, glucose, and glycerol content and the results are shown in Table 4. Ethanol increase at 24 hrs is reported with reference to the GPY10009 strain.

TABLE 4

Analysis of fermentation broth following fermentation for 24 hrs with FG, GPY10009 and GPY10009-155c at 32° C.

| Temp. (° C.) | Strain | Glucose (g/L) | Glycerol (g/L) | Ethanol (g/L) | Ethanol increase (%) |
|---|---|---|---|---|---|
| 32 | FG | 52.05 | 13.08 | 108.20 | — |
| 32 | GPY10009 | 52.81 | 12.51 | 106.72 | 1* |
| 32 | GPY10009-155c | 46.29 | 12.93 | 109.05 | 2.2 |

*nominal reference value

Yeast harboring the deletion of the gene YDR155c, and also expressing the alternative pathway, produced significantly more ethanol (i.e., in excess of 2%) compared to equivalent yeast without the YDR155c deletion at 24 hrs. Note that the GPY10009 yeast ultimately produce more ethanol at 48 hours that wild-type FG yeast (data not shown); however, they are relatively "slow starters" and produce less ethanol at 24 hours. Deletion of the YDR155c gene therefore appears to increase the initial growth rate of the GPY10009 yeast.

Example 5: Ethanol Production by Modified Yeast Expressing Glucoamylase

Yeast expressing the aforementioned CS4 variant of *Trichoderma reesei* glucoamylase and further harboring the deletion of the gene YDR155c (i.e., SA-155c) were tested for their ability to produce ethanol compared to benchmark yeast, which did not have a YDR155c deletion (i.e., SYN-ERXIA™ ADY, herein "SA," which are wild-type for the YDR155c gene) in liquefact at 32° C. for 24 hrs. Liquefact (i.e., corn flour slurry having a dry solid (ds) value of 34.3% was prepared by adding 600 ppm urea, 0.124 SAPU/g ds FERMGEN™ 2.5× (an acid fungal protease), no exogenous CS4 (a variant of *Trichoderma reesei* glucoamylase) was added and 1.46 SSCU/g ds *Aspergillus kawachii* α-amylase at pH 4.8.

5 grams of liquefact was weighted into 10 ml vessels and inoculated with fresh overnight cultures from colonies of the SA and SA-155c strain and incubated at 32° C. for 24 hrs. Samples were harvested by centrifugation, filtered through 0.2 µm filters, and analyzed for ethanol, glucose, acetate and glycerol content by HPLC (Agilent Technologies 1200 series) using Bio-Rad Aminex HPX-87H columns at 55° C., with an isocratic flow rate of 0.6 ml/min in 0.01 N $H_2SO_4$ eluent. A 2.5 µl sample injection volume was used. Calibration standards used for quantification included known amounts of DP4+, DP3, DP2, DP1, glycerol and ethanol. The results of the analyses are shown in Table 5. Ethanol increase is reported with reference to the SA strain.

TABLE 5

Analysis of fermentation broth following fermentation with SA and SA-155c strains

| Temp. (° C.) | Strain | Glucose (g/L) | Glycerol (g/L) | Acetate (g/L) | Ethanol (g/L) | Ethanol increase (%) |
|---|---|---|---|---|---|---|
| 32 | SA-155c | 67.53 | 14.61 | 0.31 | 99.35 | 4.0 |
| 32 | SA | 80.89 | 13.35 | 0.26 | 95.49 | 1* |

*nominal reference value

Yeast harboring the deletion of the gene YDR155c, and also expressing the glucoamylase, produced significantly more ethanol (i.e., about 4%) compared to the strains without the YDR155c deletion at 24 hrs.

What is claimed is:

1. Modified yeast cells derived from parental yeast cells, the modified cells comprising a genetic alteration that causes the modified cells to produce a decreased amount of functional Cpr1 polypeptide compared to the parental cells and a disruption of the YJL065c gene present in the parental cells that causes the modified cells to produce a decreased amount of functional Dls1 polypeptides compared to the parental cells, wherein the modified cells produce during fermentation an increased amount of ethanol compared to parental cells under equivalent fermentation conditions.

2. The modified cells of claim 1, wherein the genetic alteration comprises a disruption of the YDR155c gene present in the parental cells.

3. The modified cells of claim 2, wherein disruption of the YDR155c gene is the result of deletion of all or part of the YDR155c gene.

4. The modified cells of claim 2, wherein disruption of the YDR155c gene is the result of deletion of a portion of genomic DNA comprising the YDR155c gene.

5. The modified cells of claim 2, wherein disruption of the YDR155c gene is the result of mutagenesis of the YDR155c gene.

6. The modified cells of claim 1, wherein the cells do not produce functional Cpr1 polypeptides.

7. The modified cells of claim 1, wherein the cells do not produce Cpr1 polypeptides.

8. The modified cells of claim 1, wherein the cells do not produce functional Dls1 polypeptides.

9. The modified cells of claim 1, wherein the cells are of a *Saccharomyces* spp.

10. The modified cells of claim 1, wherein the amount of ethanol produced by the modified yeast cells and the parental yeast cells is measured at 24 hours following inoculation of a hydrolyzed starch substrate comprising 34-35% dissolved solids and having a pH of 4.8-5.4.

11. A method for producing a modified yeast cell comprising: introducing a genetic alteration into a parental yeast cell, which genetic alteration reduces or prevents the production of functional Cpr1 polypeptide compared to the parental cells, thereby producing modified cells that produce during fermentation an increased amount of ethanol compared to the parental cells under equivalent fermentation conditions.

12. The method of claim 11, wherein the genetic alteration comprises disrupting the YDR155c gene in the parental cells by genetic manipulation.

13. The method of claim 11, wherein the genetic alteration comprises deleting the YDR155c gene in the parental cells using genetic manipulation.

14. The method of claim 11, wherein disruption of the YDR155c gene is performed in combination with disrupting the YJL065 gene present in the parental cells.

15. The method of claim 11, wherein the modified cell is from a *Saccharomyces* spp.

16. The method of claim 11, wherein the amount of ethanol produced by the modified yeast cells and the parental yeast cells is measured at 24 hours following inoculation of a hydrolyzed starch substrate comprising 34-35% dissolved solids and having a pH of 4.8-5.4.

* * * * *